United States Patent [19]

Ryan

[11] Plant 4,419

[45] May 22, 1979

[54] WHITE ROSE SPORT NO. 72-M

[75] Inventor: Glenn H. Ryan, Pershing, Ind.

[73] Assignee: Joseph H. Hill Company, Richmond, Ind.

[21] Appl. No.: 929,580

[22] Filed: Jul. 31, 1978

[51] Int. Cl.[2] ..... A01H 5/00

[52] U.S. Cl. ..... Plt./14

[58] Field of Search ..... Plt./14

*Primary Examiner*—Robert E. Bagwill

*Attorney, Agent, or Firm*—Chas. W. Rummler

[57] ABSTRACT

A white rose plant intended for greenhouse culture and production of cut flowers distinguished by its prolific growth habits, disease resistance, and its abundant production of flowers of a medium large size offering versatility in usage for corsages, low-profile centerpieces and hospital arrangements.

1 Drawing Figure

BACKGROUND OF THE NEW PLANT

This new rose was discovered by me in greenhouse at Richmond, Ind., in December 1972 as a sport of "Tammy" (U.S. Plant Pat. No. 3,464). The attractive flower color and form led me to propagate this sport by grafting at Richmond, Ind., for test purposes and the new plant exhibited such advantageous characteristics that a program of propagation was begun to determine its stability from generation to generation. Asexual propagation of this plant through successive generations since 1974 has demonstrated that its distinctive characteristics hold true from generation to generation and appear to be firmly fixed and propagation of this new plant for commercial purposes is now being carried on by budding at Hamilton City, Calif., as well as at Richmond, Ind.

DESCRIPTION OF THE DRAWING

My new variety of rose plant is illustrated by the accompanying photographic drawing which shows a face view of a newly opened bud and of a fully opened flower, in full color, together with specimens of buds, young and mature leaves and other parts of the blooming plant.

DESCRIPTION OF THE NEW PLANT

The following is a detailed description of my new variety of rose plant based upon observations of greenhouse grown plants at Richmond, Ind., the color designations being according to Koster's Color Guide (K) and the Robert S. Wilson Horticultural Colour Chart (W) issued by The Royal Horticultural Society of London, England.

THE PLANT

Origin: Sport.
Parentage: "Tammy" (U.S. Plant Pat. No. 3,464).
Classification: Hybrid Tea.
Type: For greenhouse culture.
Form: Bush.
Growth: Free and vigorous.
Habit: Upright and much branched.
Canes: Strong and of medium diameter.
Main Stems: Color — Spinach Green 0960/2 (W) overlaid with streaks of Maroon, Plate 97 (K).
*Thorns.*—Several, of medium length. Shape: Hooked downwardly from a short, narrow base.

Color: Bright Violet, Plate 61 (K). Prickles and hairs: None.
Branches: Color — Scheeles Green 860 (W).
*Thorns.*—Several, of medium length, on each branch. Shape: Hooked downwardly from a short, narrow base. Color: Rhodonite Red 0022/3 (W).
*Prickles and hairs.*—None.
New Shoots: Nearest color — Magenta, Plate 50 (K).
*Thorns.*—Several and medium in length. Shape: Downwardly hooked from a long, narrow base. Color: Magenta, Plate 50 (K). Prickles and hairs: None.
Foliage: Quantity — Abundant.
*Leaves.*—Odd pinnate compound of 3, 5 or 7 leaflets.
*Leaflets.*—Medium-large in size. Shape: Elliptical, with a round base, acuminate apex, and simply serrate margin. Aspect: Heavy and leathery. Color: Young leaves — upper surface: Pod Green 061/2 (W) overlaid with shades of Magenta, Plate 50 (K), mostly on edge of leaf. Under surface: Nearest color — Magenta, Plate 50 (K). Mature leaves — upper surface: Nearest color — Spinach Green 0960/1 (W). Under surface: Apple Green, Plate 77 (K).
*Rachis.*—Medium heavy in size, grooved on upper side and prickly on under side.
*Stipules.*—Moderately long and narrow in width with short points turning out at an angle of less than 45°.

THE BUD

Before calyx breaks:
*Size.*—Medium large.
*Form.*—Long pointed, with a conspicuous neck and foliaceous surface appendages having slender parts extending beyond the tip of the bud a distance equal to ¼ or more of the bud length.
*Color of calyx.*—Scheeles Green 860/1 (W).
As Calyx Breaks:
*Color of outside petal.*—Chartreuse Green 663/2 (W).
As First Petal Opens:
*Bud size.*—Medium large.
*Bud form.*—Long pointed.
*Color of petal.*—Outside and inside — white, with base of Chartreuse Green 663/3 (W).

*Opening.*—The bud opens well in greenhouse.

Sepals: Permanent, spear-shaped, of moderately long length and curled.

*Inside color.*—Pod Green 061/3 (W) in center with a margin of Scheeles Green 860/1 (W) along edges.

*Outside color.*—Scheeles Green 860/3 (W).

Peduncle: Strong and erect. Of medium length and diameter.

*Bark.*—Smooth. Color: Fern Green 0862 (W).

*Thorns.*—None.

*Prickles.*—Numerous. Color: Geranium Lake 20/3 (W).

*Hairs.*—None.

THE FLOWER

Blooming Habit: Abundant and continuous.

Size of Bloom: Medium large, 2½ to 3 inches in diameter when fully opened.

Form: Full and high centered at first, with petals remaining very tightly rolled outward, becoming open and high centered at maturity with the petals loosely rolled outward.

Borne: Singly on a strong stem of medium length.

Petalage: Very double with 30 to 35 regularly arranged petals.

*Shape of petals.*—Outside petals — obovate, with mucronate apex and with one notch. Intermediate petals — obovate, with mucronate apex and some with one notch. Inside petals — obovate, with mucronate apex and with one or two notches.

*Texture.*—Moderately thick.

*Aspect.*—Satiny on inside surface and shiny on outside surface.

Color:

A. The following is a description of a rose grown in greenhouse and newly opened in March 1978.

*Outside petals.*—Outside surface: White, with Chartreuse Green 663/3 (W) at base. Inside surface: White, with Chartreuse Green 663/3 (W) at base.

*Intermediate and inside petals.*—Outside and inside surfaces: Same as the outside petals.

B. This description was made from a rose that had opened for three days in a greenhouse in January 1978.

*All petals.*—Outside surface: White, some shaded with Chartreuse Green 663/3 (W). Inside surface: White Persistence: The petals hang on and dry.

Fragrance (in greenhouse): Moderate tea.

Lasting quality: 4 to 6 days in December at living room temperatures.

REPRODUCTIVE ORGANS

Stamens: Of medium number arranged regularly about the pistils.

*Filaments.*—Medium in length and most with anthers. Color: Pure White, Plate 1 (K).

*Anthers.*—Medium large in size and all open at once. Color: Saffron Yellow 7/2 (W) with some Mimosa Yellow 602/3 (W).

*Pollen.*—Moderate in quantity. Color: Straw Yellow 604/3 (W).

*Pistils.*—Many in number.

*Styles.*—Thin and of medium length, bunched and even. Color: Creamy White, Plate 2 (K).

*Stigma color.*—Primrose Yellow 601/3 (W).

*Ovularies.*—Some protruding from calyx.

*Hips.*—None.

*Seeds.*—None.

This new variety of white rose plant is very much like its parent in that it has the same growth characteristics, form and productivity. The flower, however, is of a different coloring than that of the parent plant. In general, the new flower color in combination with the characteristics of prolific growth habits, abundant production and a flower size which offers versatility in its usage makes this new plant of considerable value for the commercial market.

I claim:

1. A new and distinctive rose cultivar substantially as herein shown and described, characterized by the attractive form and medium large size of its white flowers, its abundant production of flowers borne singly on strong stems of medium length, and its prolific habit of growth.

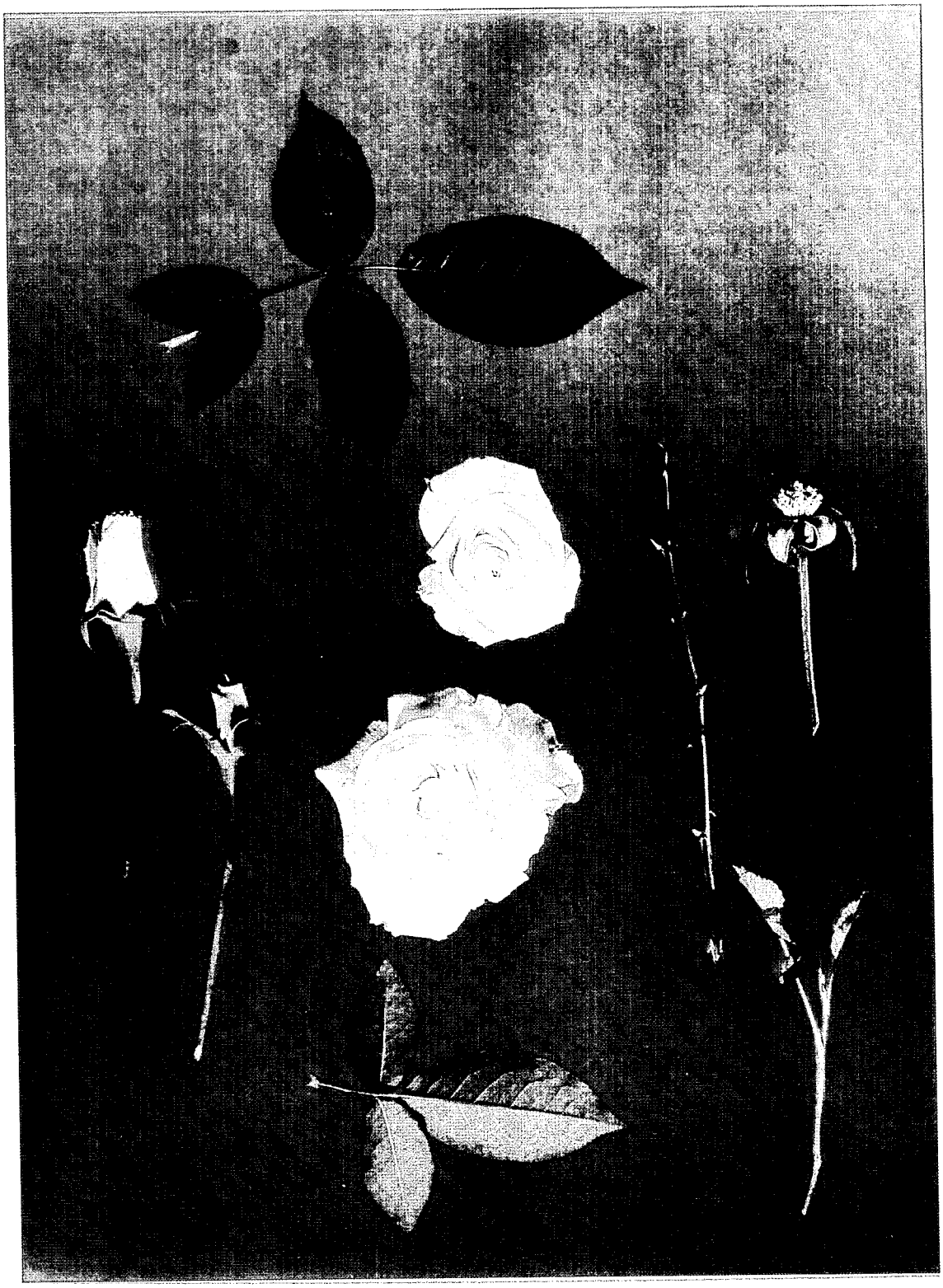

* * * * *